United States Patent [19]

Seemuth

[11] 4,405,335

[45] Sep. 20, 1983

[54] DIESEL FUEL COMPOSITION

[75] Inventor: Paul D. Seemuth, Oak Park, Mich.

[73] Assignee: Ethyl Corporation, Richmond, Va.

[21] Appl. No.: 424,054

[22] Filed: Sep. 27, 1982

[51] Int. Cl.$^3$ .............................................. C10L 1/22
[52] U.S. Cl. ......................................... 44/53; 44/56; 44/57; 44/63
[58] Field of Search .................... 44/53, 56, 57, 63; 549/476

[56] References Cited

U.S. PATENT DOCUMENTS

| | | | |
|---|---|---|---|
| 2,321,311 | 6/1943 | Mottlau et al. | 44/63 |
| 2,387,323 | 10/1945 | Gaynor et al. | 44/57 |
| 2,599,338 | 6/1952 | Lifson et al. | 44/63 |
| 2,858,200 | 10/1958 | Broughten | 44/57 |
| 3,311,559 | 3/1967 | Mottus | 44/63 |
| 3,380,815 | 4/1968 | Herbst | 44/57 |
| 4,191,536 | 3/1980 | Niebylski | 44/63 |

Primary Examiner—Charles F. Warren
Assistant Examiner—Y. Harris-Smith
Attorney, Agent, or Firm—Donald L. Johnson; John F. Sieberth; Joseph D. Odenweller

[57] ABSTRACT

The cetane rating of diesel fuel is increased by the addition of a small but effective amount of a tetrahydrofurandiol dinitrate.

3 Claims, No Drawings

DIESEL FUEL COMPOSITION

BACKGROUND

Diesel engines operate by compression ignition. They have compression ratios in the range of 14:1 to 17:1 or higher and for that reason obtain more useful work from a given amount of fuel compared to an Otto cycle engine. Historically, diesel engines have been operated on a petroleum-derived liquid hydrocarbon fuel boiling in the range of about 300°–750° F. Recently, because of dwindling petroleum reserves, alcohol and alcohol-hydrocarbon blends have been studied for use as diesel fuel.

One major factor in diesel fuel quality is cetane number. Cetane number is related to ignition delay after the fuel is injected into the combustion chamber. If ignition delays too long, the amount of fuel in the chamber increases and upon ignition results in a rough running engine and increased smoke. A short ignition delay results in smooth engine operation and decreases smoke. Commercial petroleum diesel fuels generally have a cetane number of about 40–55. Alcohols have a much lower cetane value and require the addition of a cetane improver for successful engine operation.

Through the years, many types of additives have been used to raise the cetane number of diesel fuel. These include peroxides, nitrites, nitrates, nitrosocarbamates, and the like. Alkyl nitrates such as amyl nitrate, hexyl nitrate and mixed octyl nitrates have been used commercially with good results.

SUMMARY

It has now been discovered that the cetane number of diesel fuel, both hydrocarbon and alcohol, can be increased by the addition of a tetrahydrofurandiol dinitrate.

DESCRIPTION OF PREFERRED EMBODIMENTS

A preferred embodiment of the invention is liquid fuel adapted for use in a diesel engine, said fuel being selected from the group consisting of liquid hydrocarbons of the diesel boiling range, alcohols and mixtures thereof, said fuel containing a cetane increasing amount of a tetrahydrofurandiol dinitrate cetane improver.

The tetrahydrofurandiol dinitrates have the structure

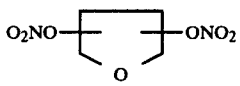

The remaining valences are bonded to hydrogen or can be substituted with other groups such as alkyl, aryl, cycloalkyl, aralkyl, halogen and the like.

Representative examples of such compounds are:
2,5-dimethyltetrahydro-3,4-furandiol dinitrate
2-isooctyltetrahydro-3,4-furandiol dinitrate
2-eicosyltetrahydro-3,4-furandiol dinitrate
2-phenyltetrahydro-3,4-furandiol dinitrate
2-benzyltetrahydro-3,4-furandiol dinitrate
2-(α-methylbenzyl)tetrahydro-3,4-furandiol dinitrate
2-chlorotetrahydro-3,4-furandiol dinitrate
2-bromotetrahydro-3,4-furandiol dinitrate
2-cyclohexyltetrahydro-3,4-furandiol dinitrate
2-(4-isobutylphenyl) tetrahydro-3,4-furandiol dinitrate
and the like.

The most preferred additive is tetrahydro-3,4-furandiol dinitrate.

The following example shows a method for making the additives by the nitration of the appropriate tetrahydrofurandiol using mixed nitric-sulfuric acid.

EXAMPLE 1

In a reaction vessel was placed a mixture of 18.7 ml. 70 percent nitric acid, 28 ml. conc. sulfuric acid and 0.23 urea. This was stirred and cooled to −10° C. at which time an equal volume mixture of methylene chloride and tetrahydro-3,4-furandiol (25 g. 0.24 mole) was added dropwise. After one-third of this solution had been added, an additional 18.6 ml. 70 percent nitric acid, 27 ml. conc. sulfuric acid and 0.23 g. urea was added. While stirring at about −10° C. the remaining solution was added dropwise. Total addition time was 1.5 hours. The mixture was stirred an additional 30 minutes at −10° C. and then poured into an ice-water mixture. The organic layer was separated and the aqueous layer extracted twice with 300 ml. portions of methylene chloride. The methylene chloride solutions were all combined and washed with aqueous sodium bicarbonate and dried over MgSO$_4$. The filtered solution was diluted further with 46.5 g. n-cetane and the methylene chloride removed under vacuum. The purpose of the added cetane was to avoid handling the pure tetrahydro-3,4-furan diol dinitrate because of a possible explosion hazard. However, the dinitrate was not soluble in n-cetane and two layers formed. The lower layer was confirmed by infrared and NMR analysis to be tetrahydro-3,4-furandiol dinitrate. The dinitrate layer (16.57 g.) was diluted with 42.98 g. methylene chloride and later a portion was added to diesel fuel for testing. The presence of the diluent was a precaution and the use of a diluent is not essential to the invention.

The amount of cetane improver added depends on the type of fuel being used, the initial cetane value, and the amount of cetane number increase desired. Alcohol fuels such as methanol, ethanol, isopropanol, isobutanol, hexanol, and the like, have very low cetane values and large amounts of cetane improvers are required. A useful range in which to operate is about 5–25 weight percent cetane improver.

Blends of alcohol and petroleum-derived diesel fuel have higher cetane values and require less cetane improver. A useful range is about 0.5–10 weight percent.

Petroleum-derived distillate fuels in the diesel boiling range require only small amounts of cetane improver to achieve a significant increase in cetane number. Such fuels without any cetane improver generally have cetane numbers in the range of about 25–60. Cetane numbers in the range of 25–35 are considered low and those in the range of 50–60 are considered top grade diesel fuels. Diesel fuels in the 35–50 mid-range are most common. An object of the invention is to upgrade the low cetane number fuels at least into the mid-range and to increase the cetane value of the mid-range fuels into the upper portion of the mid-range (e.g. 45–50) or even into the premium range above 50. It has been found that highly beneficial results can be achieved using as little as 0.05 weight percent of the present additive. Accordingly, a useful concentration range in petroleum derived diesel fuel is about 0.01–5 weight percent and more preferably about 0.05–0.5 weight percent.

The cetane increase caused by the present additives was measured using a standard cetane engine. The fuel used was a blend of 46 cetane number diesel fuel and 28 cetane number light cycle oil resulting in a 38 cetane number diesel fuel. The results are shown in the following Table.

| Concentration | Tetrahydro-3,4-furandiol Dinitrate |
|---|---|
| None | 38 |
| 0.15 wt. percent | 40.50, 40.57 |

Other conventional additives may be included in the diesel fuel including antioxidants, pour point depressants, cold filter plugging inhibitors, detergents, rust inhibitors, and the like, including other cetane improvers.

I claim:

1. Liquid fuel adapted for use in a diesel engine, said fuel being selected from the group consisting of liquid hydrocarbons of the diesel boiling range, alcohols and mixtures thereof, said fuel containing a cetane increasing amount of a tetrahydrofurandiol dinitrate cetane improver.

2. A fuel composition of claim 1 wherein said fuel is a liquid hydrocarbon of the diesel boiling range.

3. A fuel composition of claim 2 wherein said cetane improver is tetrahydro-3,4-furandiol dinitrate.

* * * * *